United States Patent [19]
Zaleski et al.

[11] Patent Number: 5,533,976
[45] Date of Patent: Jul. 9, 1996

[54] REUSABLE CARTRIDGE ASSEMBLY FOR A PHACO MACHINE

[75] Inventors: Edward R. Zaleski, Santa Ana; Mark S. Cole, Trabuco Canyon, both of Calif.

[73] Assignee: Allergan, Inc., Irvine, Calif.

[21] Appl. No.: 276,085

[22] Filed: Jul. 15, 1994

[51] Int. Cl.$^6$ .................................................. A61M 1/00
[52] U.S. Cl. ........................................................ 604/153
[58] Field of Search .......................... 604/30, 31, 32–34, 604/35, 65–67, 118, 119, 151, 153

[56] References Cited

U.S. PATENT DOCUMENTS 5,324,422  6/1994  Colleran ...................................... 210/85

FOREIGN PATENT DOCUMENTS

A0559602  8/1993  European Pat. Off. .
9312825   8/1993  WIPO .
9325874  12/1993  WIPO .
8324817  12/1993  WIPO .
9415099   7/1994  WIPO .

Primary Examiner—Randall L. Green
Assistant Examiner—Manuel Mendez
Attorney, Agent, or Firm—Walter A. Hackler

[57] ABSTRACT

A reusable cartridge assembly for a phaco machine includes a first plate with a plurality of flow channels therein and a sealing gasket with a sheet for sealing against the first plate to prevent fluid from leaving the flow channels. In addition, a tube is provided, fixed to the sealing gasket and protruding therefrom, for enabling engagement between the tube and a pump head for circulation of fluid through flow channels. A second plate is provided for applying a sealing pressure between the sheet and the first plate. In addition, the sealing gasket may include a sensing element for determining pressure within the flow channels.

30 Claims, 3 Drawing Sheets

REUSABLE CARTRIDGE ASSEMBLY FOR A PHACO MACHINE

The present invention generally relates to irrigation/aspiration apparatus for surgical procedures and more particularly relates to a cartridge assembly for a drawer-loaded cassette system for use with a surgical instrument for endophthalmic surgery.

The removal of cataracts, for example, involves surgery on a normally pressurized eye in which instruments are passed through a small incision at the edge of the cornea in order to access and remove opaque cataract material.

The cataracts may be fragmentized by cutting apparatus, vibratory apparatus, or the like, and the fragments are aspirated from the eye.

In order to maintain normal pressure within the eye, a balanced salt solution is supplied from an elevated chamber, the chamber being elevated to a position to provide proper head, or pressure.

The irrigation and aspiration of fluid through the eye must be carefully monitored in order to maintain normal pressure within the eye during surgical procedures. An under-pressure may cause distortion of the eye which often may interfere with surgical procedures. Over pressure may cause damage to the eye and in extreme cases, rupture thereof.

As it has been hereinabove noted, pressure in the eye may be controlled by the physical elevation of the chamber of balanced salt solution, which is connected to the surgical instrument. Aspiration fluid, on the other hand, is controlled in the eye with a peristaltic pump.

Typical apparatus includes instrument console for controlling the flow of fluids. Various devices have been developed for the coordinated flow of fluids and some include a phacocassette, tubing and management system, which may be disposable or autoclavable, for interconnecting from the various tubes and lines for proper irrigation and aspiration.

A general discussion of the advantages of this type of cassette is set forth in U.S. Pat. No. 4,713,051. Further descriptions of phaco apparatus are disclosed in copending U.S. patent applications, Ser. Nos. 08/105,461 now U.S. Pat. No. 5324180 and 08/201,567now U.S. Pat. No. 5470312, these disclosures being incorporated into the present application in toto by this specific reference thereto.

SUMMARY OF THE INVENTION

A reusable cartridge assembly in accordance with the present invention for a phaco machine generally includes a first plate having means therein for defining a plurality of flow channels in the first plate. A sealing-gasket is provided which includes a sheet that provides a means for sealing against the first plate to prevent the fluid from leaving the flow channels. In this manner, a plurality of sealed flow channels are provided between the first plate and the sheet. In addition, the first plate may include means for defining a cavity in the first plate, with the cavity being in fluid communication with the flow channels. Correspondingly, the sealing gasket includes a sheet means with a pressure-sensing element and a diaphragm interconnecting the sheet means and the pressure-sensing element for suspending the pressure-sensing element within the sheet means and aligning the pressure-sensing element with the cavity.

More particularly, the present invention may include tube means, fixed to the sealing gasket and protruding from the sheet for enabling engagement between the tube means and a pump head and pinch valves in order to circulate fluid through the flow channels. Additionally, a second plate means may be provided for applying a sealing pressure between the sheet means and the first plate.

In a preferred embodiment of the present invention, the second plate means comprises flow channels therein which provide a means for enabling fluid to pass from the flow channels in the first plate into the flow channels in the second plate and thereafter in and out of the tube means. In this manner, the first plate and the second plate cooperate in establishing fluid flow channels within the reusable cartridge assembly, when assembled.

More particularly, the cartridge assembly in accordance with the present invention includes a cutout portion in each of the first plate, sheet means and the second plate means for enabling the pump head to be disposed within an outside envelope of the reusable cartridge. To facilitate access to the fluid flow channels, a plurality of inlet and outlet nipples disposed on the edges of the first plate and including communication to the channels may be provided.

In one embodiment of the present invention, a pressure-sensing element may comprise a ferromagnetic disk. Alternatively, the pressure-sensing element may include a laser light reflector or an ultrasonic reflector responsive, by concomitant movement with the fluid in the cavity, for sensing pressure differential which is translated into an electrical signal corresponding thereto.

Importantly, the major elements of the present invention, namely, the first plate, the second plate and the sealing gasket are all autoclavable, i.e., capable of being sterilized with conventional autoclaving equipment so that the reusable cartridge assembly comprising the hereinabove named components may be repeatedly used.

BRIEF DESCRIPTION OF THE DRAWINGS

The advantages and features of the present invention will be better understood by the following description when considered in conjunction with the accompanying drawings in which.

DETAILED DESCRIPTION

Figure 1:
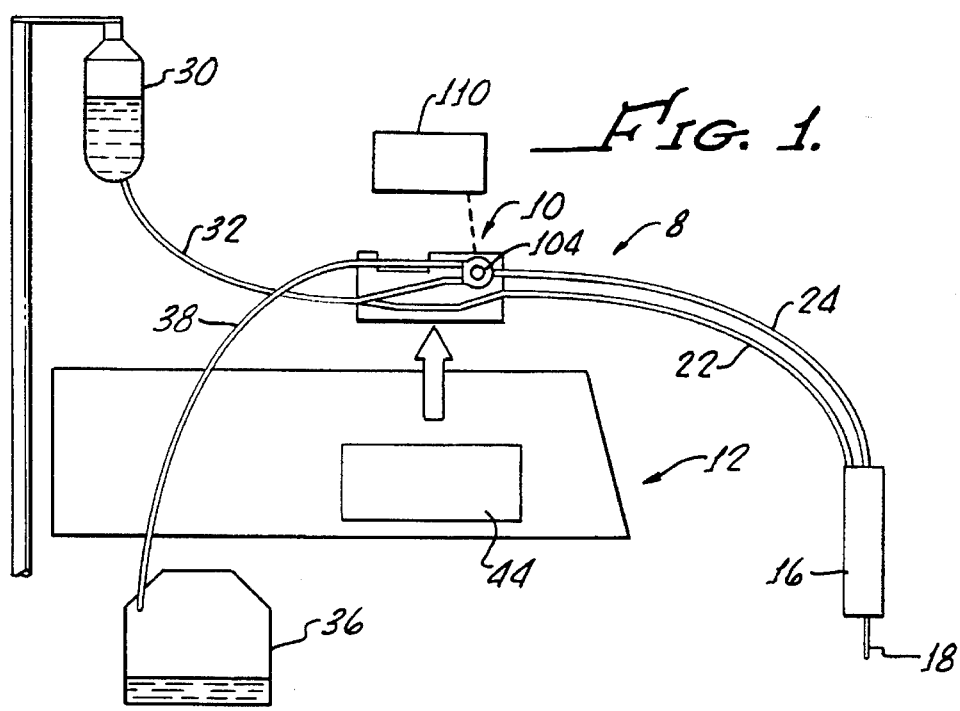
FIG. 1 is a schematic representation of the present invention illustrating its use with a surgical instrument, a saline solution supply, and a waste receptacle.

In FIG. 1, there is shown, in a conceptual format, a surgical instrument system 8, a drawer-loading reusable cartridge assembly 10, a control cabinet 12 having a pump head 14 (see FIG. 2), and a surgical instrument 16 (see FIG. 1).

Figure 2:
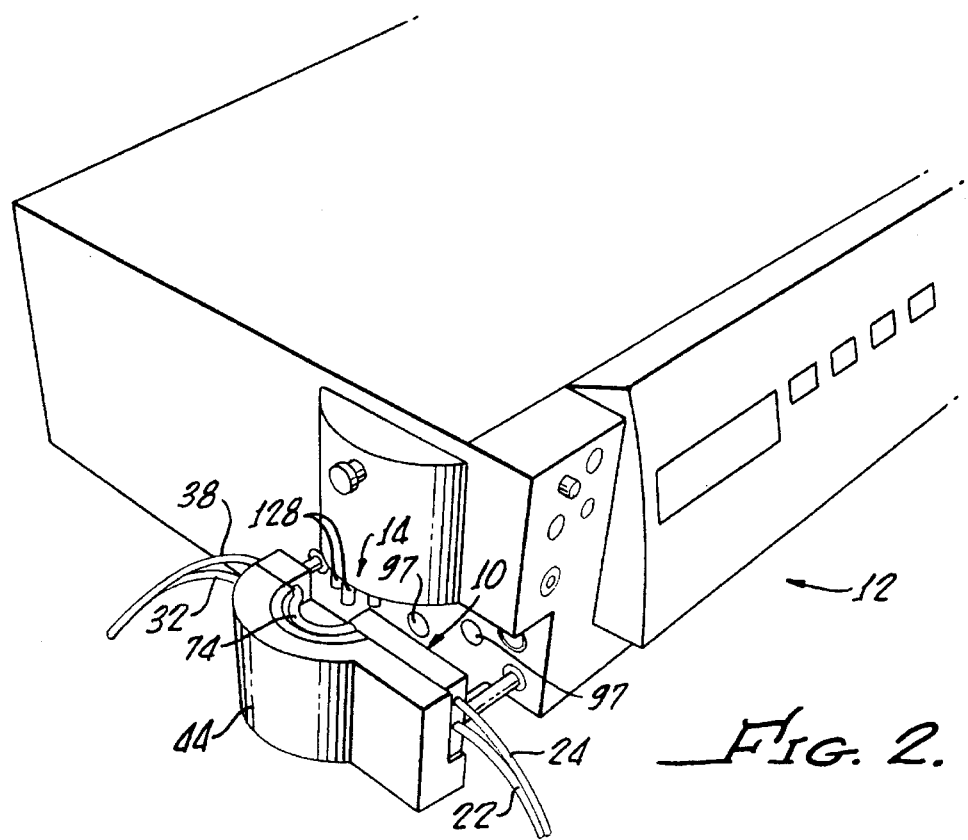
FIG. 2 is a perspective view of a cartridge assembly as it may be inserted into a drawer and control cabinet.

As hereinabove described, the present invention is used in conjunction with the surgical instrument or handpiece 16 for ophthalmic surgery, requiring irrigation and aspiration of fluids. As will be hereinafter discussed in greater detail, the reusable cartridge assembly 10 is connected with an irrigation line 22 and an aspiration line 24 for providing fluid communication between the surgical handpiece 16 and a source 30 of balanced saline solution (BSS) through a BSS line 32 and also with a waste receptacle 36 through a waste line 38. All these are diagrammatically represented in FIG. 1. As will be described hereinafter in greater detail, the reusable cartridge assembly or cassette cartridge 10 is sized for insertion into a drawer 44 in the cabinet 12 (FIG. 2).

Figures 3, 4:
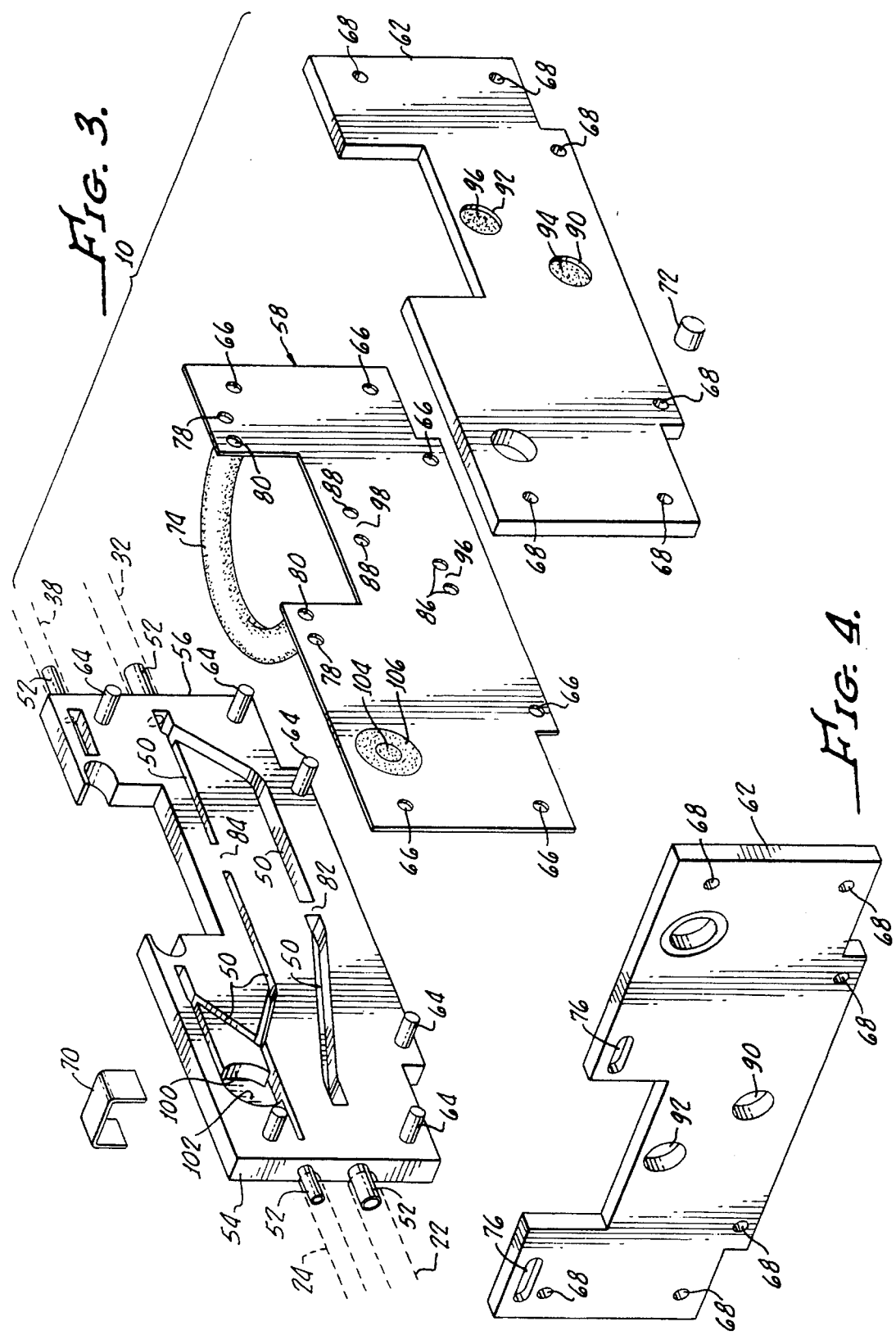
FIG. 3 is an exploded perspective view of the cartridge assembly in accordance with the present invention.
FIG. 4 is a perspective view of a second plate showing fluid flow channels therein.

Turning now to FIG. 3, the reusable cartridge assembly, or cartridge, 10 in accordance with the present invention for use in the control cabinet, or the machine, 12 generally includes the first plate 48 which is routed, or grooved to provide a means defining a plurality of flow channels 50 therein, the channels being in fluid communication with nipples 52 disposed on edges 54, 56 of the first plate 48.

A sealing gasket 58 includes a sheet 60 formed from a suitable autoclavable flexible material, provides a means for sealing against the first plate 48 to prevent the fluid from leaving the flow channels 50.

A second plate 62 provides a means for applying a sealing pressure between the sheet 60 and the first plate 48. Alignment between the first plate 48, the gasket 58 and the second plate 62 is provided by pins 64 protruding from a first plate 48 and corresponding holes 66 in the sheet 60 and holes 68 in the second plate 62. The first plate 48 and second plate 62 with the gasket 58 disposed therebetween may be held in a sealing and abutting relationship by any means such as clips 70 or pin snaps 72 for engaging the pins 64. The clamping means shown is only a specific example with any suitable means for holding the first plate 48, gasket 58 and second plate 62 being acceptable.

A tube 74 communicating with the sealing gasket 58 enables engagement between the tube 74 and the pump head 12, as hereinafter described in greater detail, for causing circulation of fluid through the flow channels 50.

As shown in FIG. 4, the second plate 62 may include flow channels 76 for enabling fluid to pass from the flow channels 50 in the first plate through holes 78 in the sheet 60 into the channels 76 and thereafter in and out of the tube 74 by holes 80 in the sheet 60.

Flow in the channels 50 may be controlled by plate portions 82, 84 and apertures 86, 88 and holes 90, 92 in the second plate 60, which may be sealed by membranes 94, 96 for enabling plungers 97 (see FIG. 2) to effect elation of fluid through the channels 50 by pressing portions 96, 98 against the plate portions 82, 84 to regulate or stop fluid flow in the channels 50. An arrangement similar to this is shown in U.S. Pat. No. 4,735,610 and 4,758,238.

Importantly, the first plate 48 is formed with a cavity 100 having a back surface 102 which is in fluid communication with the flow channels 50 for establishing a volume of fluid, and the gasket 58 includes a sensing element 104 suspended in a planar relationship therewith by a diaphragm 106 so that changes in the pressure of fluid within the cavity 100 cause the sensing element 104 and diaphragm to move in a direction perpendicular to the plane of the sheet 60 in order to provide a means for measuring the pressure of the fluid within the channels 50.

The sensing element 104 may be a ferromagnetic disk which is coupled to a measuring device 110 (see FIG. 1) which may be a transducer as described in U.S. patent application Ser. No. 07/893,119, filed Feb. 25, 1994. This reference is incorporated herewith by this reference thereto for teaching the manner in which the ferromagnetic disk may be coupled to a force transducer.

Alternatively, the sensing element 104 may be a laser light reflector or an ultrasound reflector and the measuring element 110 correspondingly may be a laser detector or ultrasound detector.

Figure 5:
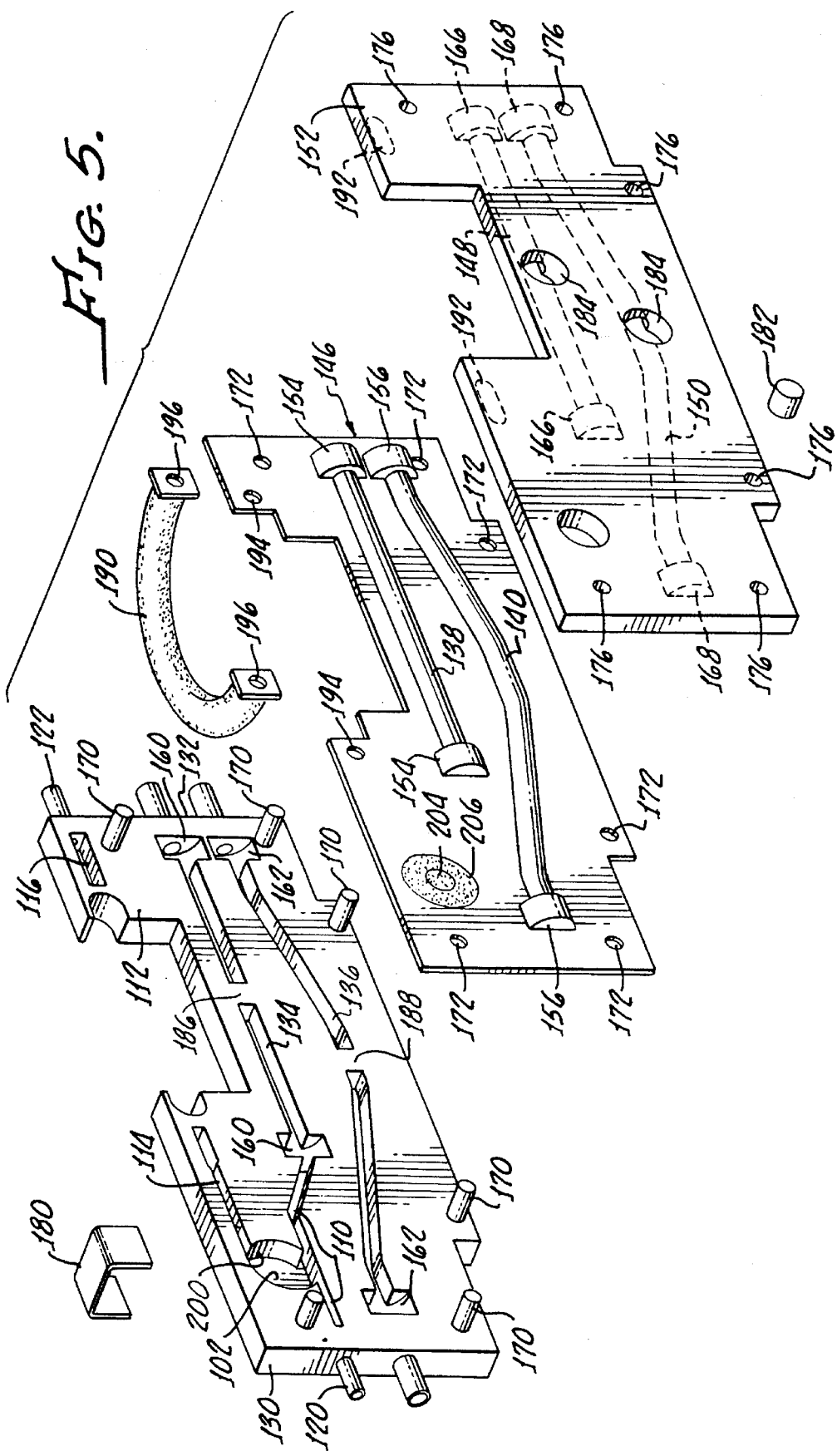
FIG. 5 is an exploded perspective view of an alternative embodiment of the present invention in which a gasket includes conduits therein for the flow of fluids therethrough.

Turning now to FIG. 5, an alternative embodiment 110 in accordance with the present invention generally includes a first plate 112 which is routed, or grooved, to provide a means defining a plurality of flow channels 114, 116 which are in fluid communication with nipples 120, 122 disposed on edges 130, 132 of the first plate 112. In addition, grooves 134, 136 may be provided for accommodating conduits 138, 140 formed in a gasket sheet 146. The conduits 138, 140 may be integrally formed into the gasket 146 or adhered thereto in a manner providing for protrusion of the conduits 138, 140 on either side of the sheet gasket 146 for acceptance into the channels 134, 136 of the first plate and channels 148, 150 in a second plate 152. The conduits 138 may terminate in mini manifolds 154, 156 which are sized for acceptance into indentations 160, 162 in the first plate 112 and 166, 168 in the second plate 152.

The second plate 152 provides means for providing a sealing pressure to the sheet 146 and the first plate 112. Alignment between the first plate 112, the gasket 146 and the second plate 152 is provided by pins 170 protruding from the first plate and corresponding holes 172 in the sheet 146 and holes 176 in the second plate 152. The first plate 116 and second plate 152 may be held in a sealing and abutting relationship by any means such as clips 180 or pin snaps 182 or engagement pins 170. Openings 184 in the second plate provide a means for enabling plunger 97 access to the gasket conduits 138, 140 in order to regulate fluid flow therein by forcing same against berms 86, 88 formed in the grooves 134, 136 respectively.

A tube 190 communicating with the sealing gasket 146 enables engagement between the tube 190 and the pump head 12, as hereinbefore described in connection with embodiment 10. It should be noted that while the tube 74 may be fixed to the gasket 58 as shown in FIG. 3, alternatively, the tube 190 may be separate from the gasket 146 but in communication therewith when tube 190 ends are held in alignment with the gasket 190 by the first plate 112, and the second plate 152.

Similar to the embodiment 10, the second plate 152 may include flow channels 192 for enabling fluid to pass from flow channels 114, 116 in the first plate 112 through holes 194 in the sheet 146 into the channels 192 and thereafter in and out of the tube 190 by holes 196 in the sheet 146.

Similar to the embodiment shown in FIG. 3, the first plate 112 of the second embodiment 110 is formed with a cavity 200 having a back surface 202 which is in fluid communication with the flow channels 114 for establishing a volume of fluid, and the gasket 148 includes a sensing element 204 suspended in a planar relationship therewith by a diaphragm 206 so that changes in the pressure of fluid within the cavity 200 cause a sensing element 204 and diaphragm 206 to move in a direction perpendicular to the plane of the sheet 146 in order to provide a means for measuring the pressure of the fluid within the channels 114.

As hereinbefore described, the sensing element 204 may be a ferromagnetic disk, a laser-like reflector, or an ultrasound reflector.

Although there has been hereinabove described a reusable cartridge assembly for a phaco machine, in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. A reusable cartridge assembly for a phaco machine, said reusable cartridge assembly comprising:

a first plate having means for defining a plurality of flow channels therein;

a sealing gasket including sheet means for sealing against said first plate to prevent fluid from leaving said flow channels, and tube means, communicating with said sealing gasket and protruding from the sheet means, for enabling engagement between said tube means and a pump head in order to circulate fluid through the flow channels; and second plate means for supplying a sealing pressure between the sheet means and the first plate.

2. The reusable cartridge assembly according to claim 1 wherein said second plate means comprises means, defining flow channels therein, for enabling fluid to pass from the flow channels in said first plate into the flow channels in said second plate means and thereafter into and out of the tube means.

3. The reusable cartridge assembly according to claim 2 means, comprising a cutout portion in each of the first plate, sheet means and second plate means, for enabling the pump head to be disposed within an outside envelope of the reusable cartridge.

4. The reusable cartridge assembly according to claim 3 wherein said flow channels in said first plate are in fluid communication with inlet and outlet nipples disposed on edges of said first plate.

5. The reusable cartridge assembly according to claim 4 wherein said first plate further comprises means for defining a cavity in said first plate, said cavity being in fluid communication with said flow channels in the first plate, and said sealing gasket further comprises a pressure-sensing element and diaphragm means for suspending the pressure-sensing element within the sheet means and aligned with said cavity.

6. The reusable cartridge assembly according to claim 5 wherein said second plate means comprises means, defining openings therein, for enabling plunger access to the sealing gasket and flow channels in order to regulate fluid flow therein.

7. The reusable cartridge assembly according to claim 5 wherein the pressure-sensing element comprises a ferromagnetic disk.

8. The reusable cartridge assembly according to claim 5 wherein the pressure-sensing element comprises a laser light reflector.

9. The reusable cartridge assembly according to claim 5 wherein the pressure-sensing element comprises an ultrasound reflector.

10. The reusable cartridge assembly according to claim 5 wherein said diaphragm means surrounds said pressure-sensing element.

11. A reusable cartridge assembly for a phaco machine, said reusable cartridge assembly comprising:

a first plate having means for defining a plurality of flow channels therein and means for defining a cavity in said first plate, said cavity being in fluid communication with said flow channels;

a sealing gasket including sheet means for sealing against said first plate to prevent fluid from leaving said flow channels, a pressure-sensing element and diaphragm means for suspending the pressure-sensing element within the sheet means and aligned with said cavity; and second plate means for applying a sealing pressure between the sheet means and the first plate.

12. The reusable cartridge assembly according to claim 11 wherein the pressure-sensing element comprises a ferromagnetic disk.

13. The reusable cartridge assembly according to claim 11 wherein the pressure-sensing element comprises a laser light reflector.

14. The reusable cartridge assembly according to claim 11 wherein the pressure-sensing element comprises an ultrasound reflector.

15. The reusable cartridge assembly according to claim 11 wherein said diaphragm means surrounds said pressure-sensing element.

16. The reusable cartridge assembly according to claim 11 further comprising a tube and means, attaching said tube to the sheet means, for enabling engagement between said tube and a pump head in order to circulate fluid through the flow channels.

17. The reusable cartridge assembly according to claim 16 wherein said second plate means comprises means, defining flow channels therein, for enabling fluid to pass from the flow channels in said first plate into the flow channels in said second plate means and thereafter into and out of the tube means.

18. The reusable cartridge assembly according to claim 17 means, comprising a cutout portion in each of the first plate, sheet means and second plate means, for enabling the pump head to be disposed within an outside envelope of the reusable cartridge.

19. The reusable cartridge assembly according to claim 18 wherein said flow channels in said first plate are in fluid communication with inlet and outlet nipples disposed on edges of said first plate.

20. A reusable cartridge assembly for a phaco machine, said reusable cartridge assembly comprising:

a first plate having means for defining at least one channel therein;

a sealing gasket including sheet means for sealing against said first plate means, defining at least one conduit therein, for enabling fluid to circulate through the sealing gasket and tube means fixed to said sealing gasket and protruding from the sheet means, for enabling engagement between said tube means and a pump head in order to circulate fluid through the gasket conduit and second plate means for supplying a sealing pressure between the sheet means and the first plate.

21. The reusable cartridge assembly according to claim 20 wherein said first plate further comprises means for defining a plurality of flow channels therein, and said sealing gasket means further comprises portions thereof for preventing fluid from leaving said flow channels.

22. The reusable cartridge assembly according to claim 20 wherein said second plate means comprises means, defining openings therein, for enabling plunger access to the gasket conduit in order to regulate fluid flow therein.

23. The reusable cartridge assembly according to claim 21 wherein said second plate means comprises means, defining flow channels therein, for enabling fluid to pass from the flow channels in said first plate into the flow channels in said second plate means and thereafter into and out of the tube means.

24. The reusable cartridge assembly according to claim 23 means, comprising a cutout portion in each of the first plate, sheet means and second plate means, for enabling the pump head to be disposed within an outside envelope of the reusable cartridge.

25. The reusable cartridge assembly according to claim 24 wherein said flow channels in said first plate are in fluid communication with inlet and outlet nipples disposed on edges of said first plate.

26. The reusable cartridge assembly according to claim 25 wherein said first plate further comprises means for defining a cavity in said first plate, said cavity being in fluid communication with said flow channels in the first plate, and said sealing gasket further comprises a pressure-sensing element and diaphragm means for suspending the pressure-sensing element within the sheet means and aligned with said cavity.

27. The reusable cartridge assembly according to claim 25 wherein the pressure-sensing element comprises a ferromagnetic disk.

28. The reusable cartridge assembly according to claim 25 wherein the pressure-sensing element comprises a laser light reflector.

29. The reusable cartridge assembly according to claim 25 wherein the pressure-sensing element comprises an ultrasound reflector.

30. The reusable cartridge assembly according to claim 25 wherein said diaphragm means surrounds said pressure-sensing element.

* * * * *